(12) United States Patent
Mackey et al.

(10) Patent No.: US 7,041,369 B1
(45) Date of Patent: May 9, 2006

(54) MELT PROCESSABLE STARCH COMPOSITION

(75) Inventors: Larry Neil Mackey, Fairfield, OH (US); Michael David James, Cincinnati, OH (US); Gregory Charles Gordon, Cincinnati, OH (US); John Gerhard Michael, Cincinnati, OH (US); Paul Dennis Trokhan, Hamilton, OH (US); Valerie Ann Bailey, Florence, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/220,573

(22) PCT Filed: Nov. 27, 2000

(86) PCT No.: PCT/US00/32146

§ 371 (c)(1),
(2), (4) Date: Dec. 10, 2002

Related U.S. Application Data

(63) Continuation-in-part of application No. PCT/IB00/00233, filed on Mar. 7, 2000, which is a continuation-in-part of application No. 09/264,401, filed on Mar. 8, 1999, now abandoned, and a continuation-in-part of application No. PCT/IB00/00234, filed on Mar. 7, 2000, which is a continuation-in-part of application No. 09/264,401, filed on Mar. 8, 1999, now abandoned.

(51) Int. Cl.
*C08B 30/00* (2006.01)
*C08B 31/00* (2006.01)
*C08L 3/00* (2006.01)

(52) U.S. Cl. ............... 428/373; 127/29; 127/32; 127/67; 127/71; 523/220; 524/47; 521/109.1

(58) Field of Classification Search ............. 428/373; 524/47; 523/220; 127/32, 67, 71, 29; 521/109.1
See application file for complete search history.

(56) References Cited

U.S. PATENT DOCUMENTS

| | | |
|---|---|---|
| 1,856,401 A | 5/1932 | Prince |
| 1,885,256 A | 11/1932 | Gull |
| 2,570,449 A | 10/1951 | Horsak |
| 2,902,336 A | 9/1959 | Hiemstra et al. |
| 3,117,014 A | 1/1964 | Klug |
| 3,137,592 A | 6/1964 | Protzman et al. |
| 3,280,229 A | 10/1966 | Simons |
| 3,379,811 A | 4/1968 | Hartmann et al. |
| 3,499,074 A | 3/1970 | Barger et al. |
| 3,954,361 A | 5/1976 | Page |
| 4,069,177 A | 1/1978 | Smith |
| 4,076,663 A | 2/1978 | Masuda et al. |
| 4,115,332 A | 9/1978 | Young et al. |
| 4,117,222 A | 9/1978 | Holst et al. |
| 4,139,699 A | 2/1979 | Hernandez et al. |
| 4,243,480 A | 1/1981 | Hernandez et al. |
| 4,340,563 A | 7/1982 | Appel et al. |
| 4,380,570 A | 4/1983 | Schwarz |
| 4,627,811 A | 12/1986 | Greiser et al. |
| 4,673,438 A | 6/1987 | Wittwer et al. |
| 4,818,463 A | 4/1989 | Buehning |
| 4,826,415 A | 5/1989 | Mende |
| 4,853,168 A | 8/1989 | Eden et al. |
| 4,855,179 A | 8/1989 | Bourland et al. |
| 4,900,361 A | 2/1990 | Sachetto et al. |
| 5,079,354 A | 1/1992 | Gross et al. |
| 5,095,054 A | 3/1992 | Lay et al. |
| 5,122,048 A | 6/1992 | Deeds |
| 5,234,977 A | 8/1993 | Bastioli et al. |
| 5,275,774 A | 1/1994 | Bahr et al. |
| 5,277,761 A | 1/1994 | Van Phan et al. |
| 5,280,055 A | 1/1994 | Tomka |
| 5,286,770 A | 2/1994 | Bastioli et al. |
| 5,288,765 A | 2/1994 | Bastioli et al. |
| 5,314,934 A | 5/1994 | Tomka |
| 5,316,578 A | 5/1994 | Buehler et al. |
| 5,346,936 A | 9/1994 | Buehler et al. |
| 5,362,777 A | 11/1994 | Tomka |
| 5,368,690 A | 11/1994 | Solarek et al. |
| 5,382,611 A | 1/1995 | Stepto et al. |

(Continued)

FOREIGN PATENT DOCUMENTS

EP     0 108 364 B1     8/1986

(Continued)

OTHER PUBLICATIONS

A.J.F. de Carvalho, A.A.S. Curvelo, J.A.M. Agnelli, A First Insight on Composites of Thermoplastic Starch and Kaolin, Carbohydrate Polymers 45 (2001) 189-194, received Sep. 23, 1999; revised Jan. 26, 2000, 2001 Elsevier Science Ltd.

(Continued)

*Primary Examiner*—Ana Woodward
(74) *Attorney, Agent, or Firm*—David M. Weirich; C. Brant Cook; Vlad Vitenberg

(57) ABSTRACT

The present invention relates to starch compositions which contain starch and additives. The starch has a weight average molecular weight ranging from about 1,000 to about 2,000,000. The additives can be plasticizers or diluents. The composition containing the starch and the additive is formed by means of passing the composition through a die to produce fibers, foams or films. These compositions have an extensional viscosity in the range from about 50 to about 20,000 pascal seconds. The starch compositions preferably contain a polymer that is substantially compatible with starch and has a weight-average molecular weight of at least 500,000.

16 Claims, 3 Drawing Sheets

U.S. PATENT DOCUMENTS

| | | | |
|---|---|---|---|
| 5,405,564 A | 4/1995 | Stepto et al. | |
| 5,420,180 A | 5/1995 | Katayama et al. | |
| 5,425,987 A | 6/1995 | Shawver et al. | |
| 5,427,614 A | 6/1995 | Wittwer et al. | |
| 5,444,113 A | 8/1995 | Sinclair et al. | |
| 5,446,140 A | 8/1995 | Maheras et al. | |
| 5,462,982 A | 10/1995 | Bastioli et al. | |
| 5,476,616 A | 12/1995 | Schwarz | |
| 5,480,923 A | 1/1996 | Schmid et al. | 524/47 |
| 5,516,815 A | 5/1996 | Buehler et al. | 523/128 |
| 5,679,145 A | 10/1997 | Andersen et al. | |
| 5,693,279 A | 12/1997 | Feuer et al. | |
| 5,703,160 A | 12/1997 | Dehennau et al. | |
| 5,705,536 A | 1/1998 | Tomka | |
| 5,720,832 A | 2/1998 | Minto et al. | |
| 5,736,586 A | 4/1998 | Bastioli et al. | |
| 5,773,495 A | 6/1998 | Haschke et al. | |
| 5,844,023 A | 12/1998 | Tomka | |
| 5,866,251 A | 2/1999 | Bastioli et al. | |
| 5,874,486 A | 2/1999 | Bastioli et al. | |
| 5,945,480 A | 8/1999 | Wang et al. | |
| 6,013,223 A | 1/2000 | Schwarz | |
| 6,045,908 A | 4/2000 | Nakajima et al. | |
| 6,096,809 A | 8/2000 | Lorcks et al. | |
| 6,117,925 A | 9/2000 | Tomka | |
| 6,214,907 B1 | 4/2001 | Tomka | |
| 6,218,321 B1 | 4/2001 | Lorcks et al. | |
| 6,231,970 B1 | 5/2001 | Andersen et al. | |
| 6,235,815 B1 | 5/2001 | Loercks et al. | |
| 6,235,816 B1 | 5/2001 | Lorcks et al. | |
| 6,235,835 B1 | 5/2001 | Niessner et al. | |
| 6,238,520 B1 | 5/2001 | Greenwood | |
| 6,242,102 B1 | 6/2001 | Tomka | |
| 6,277,899 B1 | 8/2001 | Bastioli et al. | |
| 6,302,997 B1 | 10/2001 | Hurter et al. | |
| 6,303,000 B1 | 10/2001 | Floyd et al. | |
| 6,365,002 B1 | 4/2002 | Bindzus et al. | |
| 6,365,079 B1 | 4/2002 | Winkler et al. | |
| 6,372,361 B1 | 4/2002 | Mackewicz et al. | |
| 6,472,497 B1 | 10/2002 | Loercks et al. | |
| 6,506,824 B1 | 1/2003 | Bastioli et al. | |
| 6,517,678 B1 | 2/2003 | Shannon et al. | |
| 2002/0015854 A1 | 2/2002 | Billmers et al. | |
| 2002/0170693 A1 | 11/2002 | Merrette et al. | |
| 2003/0022581 A1 | 1/2003 | Tsai et al. | |
| 2003/0072731 A1 | 4/2003 | Gulian et al. | |
| 2003/0099692 A1 | 5/2003 | Lydzinski et al. | |

FOREIGN PATENT DOCUMENTS

| | | |
|---|---|---|
| EP | 0 232 121 A2 | 8/1987 |
| EP | 0 080 382 B1 | 8/1988 |
| EP | 0 327 505 A | 8/1989 |
| EP | 0 327 505 B2 | 8/1989 |
| EP | 0 522 358 A | 1/1993 |
| EP | 0 522 358 A2 | 1/1993 |
| EP | 0522358 | 1/1993 |
| EP | 0 541 050 A2 | 5/1993 |
| EP | 0541050 | 5/1993 |
| EP | 0 865 841 B1 | 9/1998 |
| EP | 1 035 163 A2 | 9/2000 |
| EP | 1 035 239 A2 | 9/2000 |
| EP | 1035163 | 9/2000 |
| EP | 1 103 655 A1 | 5/2001 |
| EP | 0 722 980 B1 | 11/2001 |
| GB | 1247474 | 9/1971 |
| JP | 61040341 | 2/1986 |
| JP | 62028410 | 2/1987 |
| JP | 4100913 | 4/1992 |
| JP | 4146217 | 5/1992 |
| JP | 6212594 | 8/1994 |
| JP | 06-269239 | 9/1994 |
| JP | 8027627 | 1/1996 |
| JP | 8260250 | 10/1996 |
| JP | 09-041224 | 2/1997 |
| JP | 9276331 | 10/1997 |
| JP | 10008364 | 1/1998 |
| WO | WO 98/40434 | 9/1998 |
| WO | WO 00/43423 | 7/2000 |
| WO | WO 01/38635 | 5/2001 |
| WO | WO 01/49912 A1 | 7/2001 |

OTHER PUBLICATIONS

W. John G. McCulloch, Ph.D., The History of the Development of Melt Blowing Technology, INJ Spring 1999, pp. 66-72.

Auther Unknown, A New Crop of Nonwovens, Nonwovens Industry, Feb. 2000, p. 58.

Susanna Schiemer, Biodegradable Cellulose Fiber, Nonwovens World, Oct.-Nov. 1999, pp. 71-74.

H. Dale Wilson, Novel Polypropylene Resins for Nonwovens, Nonwovens World Oct.-Nov. 1999, p. 76.

Jan H. Schut, The New Look in Plastic—It's Paper!, Plastics Technology, Feb. 2000, pp. 52-57.

Josef L. Kokin, Lih-Shiuh Lai, Lisa L. Chedid, Effect of Starch Structure on Starch Rheological Properties, Food Technology, Jun. 1992, pp. 130-138.

Ralph D. Waniska and Marta H. Gomez, Dispersion Behavior of Starch, source unknown.

D.H. Muller, A. Krobjilowski, Meltblown Fabrics from Biodegradable Polymers, International Nonwovens Journal (Mar. 2001); abstract only.

S. Simmons et al., Thermoplastic Processing of Starch: Melt-Spinning of Starch-Based Fibers, Biodegradable Polymer Packaging (1993), Conference Proceedings, Publisher: Technomic, Lancaster, PA, pp. 171-207.

MELT PROCESSABLE STARCH COMPOSITION

CROSS REFERENCE TO RELATED APPLICATION

This application is a 371 national stage application of PCT/US00/32146 designating the United States, filed on Nov. 27, 2000, which is a continuation-in-part of PCT/IB00/00233 designating the United States, filed on Mar. 7, 2000, which is a continuation-in-part of application Ser. No. 09/264,401 filed on Mar. 8, 1999, and a continuation-in-part of PCT/IB00/00234 designating the United States, filed on Mar. 7, 2000, which is a continuation-in-part of application Ser. No. 09/264,401 filed on Mar. 8, 1999.

FIELD OF INVENTION

This invention relates a novel starch composition that is substantially homogenous and has desirable rheological characteristics such that it is melt processable by conventional thermoplastic processing equipment. The present composition is particularly suitable for uniaxial and biaxial extensional processes.

BACKGROUND OF THE INVENTION

It is well recognized that starch molecules come in two forms: the substantially linear amylose polymer and the highly branched amylopectin polymer. These two forms of starch have very different properties, probably due to the ease of association of the hydroxyl groups among different molecules. The molecular structure of amylose is essentially linear with two to five relatively long branches. The average degree of polymerization of the branches is about 350 monomer units. Under conditions that provide sufficient freedom of molecular movements, primarily by dilution with suitable solvents, and in some instances, dilution coupled with heating, the linear amylose chains can be oriented into preferentially parallel alignments such that the hydroxyl groups on one chain are in close proximity with those on the adjacent chains. The alignment of neighboring amylose molecules is believed to facilitate intermolecular hydrogen bonding. Consequently the amylose molecules form strong aggregates. In contrast, the molecular structure of amylopectin is highly branched via 1,6-α linkages. The average degree of polymerization of the branches is about 25 monomer units. Due to the highly branched structure, the amylopectin molecules can not move as freely and do not align and associate as readily.

Attempts have been made to process natural starch on standard equipment and with existing technology known in the plastic industry. Since natural starch generally has a granular structure, it needs to be "destructurized" and/or modified before it can be melt processed like a thermoplastic material. For destructurization, the starch is typically heated above its softening and melting temperature under a pressurized condition. Melting and disordering of the molecular structure of the starch granule takes place and a destructurized starch is obtained. Chemical or enzymatic agents may also be used to destructurize, oxidize, or derivatize the starch. Modified starches have been used to make biodegradable plastics, wherein the modified starch is blended as an additive or the minor component with petroleum-based or synthetic polymers. However, when the modified starch is processed by itself or as the major component in a blend with other materials using conventional thermoplastic processing techniques, such as molding or extrusion, the finished parts tend to have a high incidence of defects. Moreover, the modified starch (alone or as the major component of a blend) has been found to have poor melt extensibility; consequently, it heretofore has not been successfully processed by uniaxial or biaxial extensional processes into fibers, films, foams or the like.

Previous attempts to produce starch fibers relate principally to wet-spinning processes. For example, a starch/solvent colloidal suspension can be extruded from a spinneret into a coagulating bath. This process relies on the marked tendency of amylose to align and form strongly associated aggregates to provide strength and integrity to the final fiber. Any amylopectin present is tolerated as an impurity that adversely affects the fiber spinning process and the strength of the final product. Since it is well known that natural starch is rich in amylopectin, earlier approaches include pre-treating the natural starch to obtain the amylose-rich portion desirable for fiber spinning. Clearly this approach is not economically feasible on a commercial scale since a large portion (i.e., the amylopectin portion) of the starch is discarded. In more recent developments, natural starch, typically high in natural amylopectin content, can be wet-spun into fibers. However, the wet-spun fibers are coarse, typically having fiber diameters greater than 50 microns. Additionally, the large quantity of solvent used in this process requires an additional drying step and a recovery or treatment step of the effluent. Some references for wet-spinning starch fibers include U.S. Pat. No. 4,139,699 issued to Hernandez et al. on Feb. 13, 1979; U.S. Pat. No. 4,853,168 issued to Eden et al. on Aug. 1, 1989; and U.S. Pat. No. 4,234,480 issued to Hernandez et al. on Jan. 6, 1981.

U.S. Pat. Nos. 5,516,815 and 5,316,578 to Buehler et al. relate to starch compositions for making starch fibers from a melt spinning process. The melt starch composition is extruded through a spinnerette to produce filaments having diameters slightly enlarged relative to the diameter of the die orifices on the spinnerette (i.e., a die swell effect). The filaments are subsequently drawn down mechanically or thermomechanically by a drawing unit to reduce the fiber diameter.

Other thermoplastically processable starch compositions are disclosed in U.S. Pat. No. 4,900,361, issued on Aug. 8, 1989 to Sachetto et al.; U.S. Pat. No. 5,095,054, issued on Mar. 10, 1992 to Lay et al.; U.S. Pat. No. 5,736,586, issued on Apr. 7, 1998 to Bastioli et al.; and PCT publication WO 98/40434 filed by Hanna et al. published Mar. 14, 1997.

SUMMARY OF THE INVENTION

The present invention relates to a starch composition that is melt processable on conventional thermoplastic equipment. Specifically, the starch composition may be successfully processed via uniaxial or biaxial extensional forces to provide a final product with good strength. Moreover the starch composition has rheological properties suitable for use in melt attenuation processes to achieve very high uniaxial or biaxial extensions.

The present invention relates to a starch composition which exhibits an extensional viscosity ranging from about 50 to about 20,000 pascal•seconds and which has a capillary number of at least 1. In one embodiment, the starch compositions of the present invention incorporates a polymer that is substantially compatible with starch and has a weight-average molecular weight of at least 500,000. The starch composition may also desirably contain an additive to enhance melt flow and/or melt processability.

DETAILED DESCRIPTION OF THE INVENTION

Figure 1:
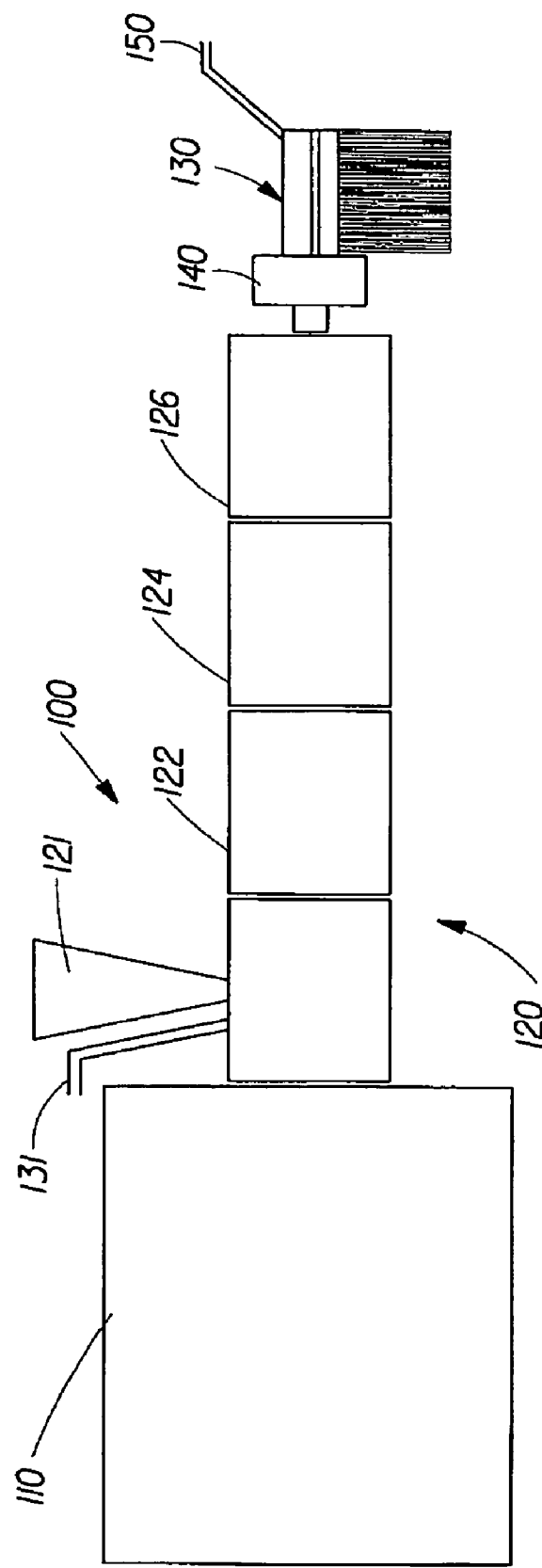
FIG. 1 shows a torque rheometer assembly having a melt blowing die which may be used to produce fine starch fibers of the present invention.
Figure 2:
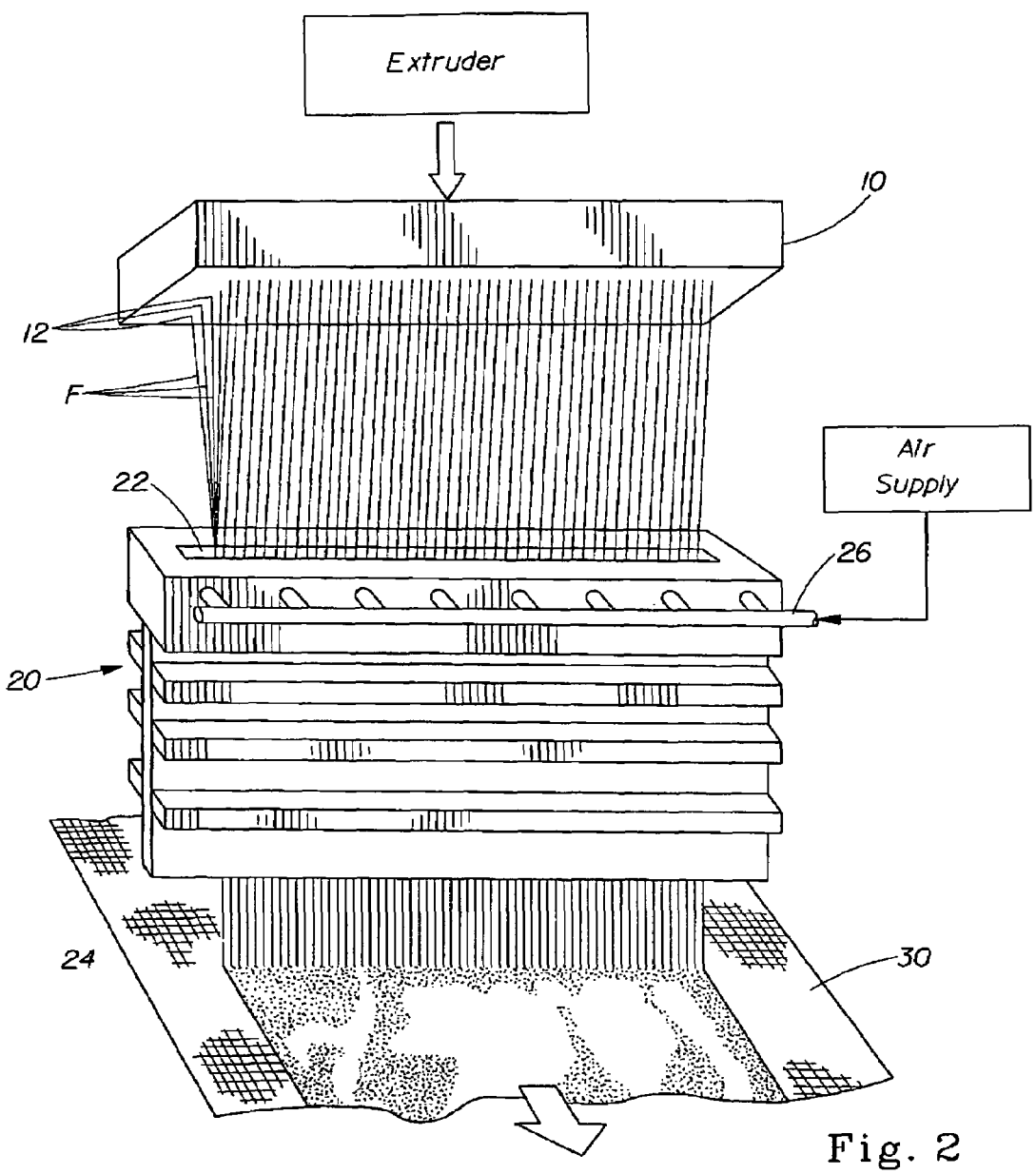
FIG. 2 shows a torque rheometer assembly which may be used to produce starch fiber web by spun bonding.

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, the term "bound water" means the water found naturally occurring in starch before starch is mixed with other components to make the composition of the present invention. The term "free water" means the water that is added in making the starch composition of the present invention. A person of ordinary skill in the art would recognize that once the components are mixed in a composition, water can no longer be distinguished by its origin. Therefore, the water in a composition includes all water, regardless of the source.

All percentages, ratios and proportions used herein are by weight percent of the composition, unless otherwise specified.

The Starch Compositions

It has been discovered by Applicants that, surprisingly, starch compositions which exhibit certain rheological behaviors can be melt processed on conventional thermoplastic equipment to produce useful fibers, filaments, foams or films. The compositions herein comprise a starch and, in certain preferred embodiments, a high molecular weight polymer and/or additives.

I. The Ingredients

A. The Starch

Naturally occurring starch is generally a mixture of linear amylose and branched amylopectin polymer of D-glucose units. The amylose is a substantially linear polymer of D-glucose units joined by (1,4)-α-D links. The amylopectin is a highly branched polymer of D-glucose units joined by (1,4)-α-D links and (1,6)-α-D links at the branch points. Naturally occurring starch typically contains relatively high levels of amylopectin, for example, corn starch (64–80% amylopectin), waxy maize (93–100% amylopectin), rice (83–84% amylopectin), potato (about 78% amylopectin), and wheat (73–83% amylopectin). Though all starches are potentially useful herein, the present invention is most commonly practiced with high amylopectin natural starches derived from agricultural sources, which offer the advantages of being abundant in supply, easily replenishable and inexpensive.

As used herein, "starch" includes any naturally occurring unmodified starches, modified starches, synthetic starches and mixtures thereof, as well as mixtures of the amylose or amylopectin fractions; the starch may be modified by physical, chemical, or biological processes, or combinations thereof. The choice of unmodified or modified starch for the present invention may depend on the end product desired. In one embodiment of the present invention, the starch or starch mixture useful in the present invention has an amylopectin content from about 20% to about 100%, more typically from about 40% to about 90%, even more typically from about 60% to about 85% by weight of the starch or mixtures thereof.

Suitable naturally occurring starches can include, but are not limited to, corn starch, potato starch, sweet potato starch, wheat starch, sago palm starch, tapioca starch, rice starch, soybean starch, arrow root starch, amioca starch, bracken starch, lotus starch, waxy maize starch, and high amylose corn starch. Naturally occurring starches particularly, corn starch and wheat starch, are the preferred starch polymers due to their economy and availability.

Physical modifications of the starch may be intramolecular or intermolecular modifications. Intramolecular modifications include reduced molecular weight and/or molecular weight distribution, changes in the polymer chain conformation, and the like. Intermolecular modifications include melting and/or disordering the starch molecules, reduction in crystallinity, crystallite size, and granular size, and the like. These physical modifications may be achieved by input of energy (such as thermal, mechanical, thermomechanical, electromagnetic, ultrasonic, and the like), pressure, moisture, fractionation, and combinations thereof.

Chemical modifications of starch typically include acid or alkali hydrolysis and oxidative chain scission to reduce molecular weight and molecular weight distribution. Suitable compounds for chemical modification of starch include organic acids such as citric acid, acetic acid, glycolic acid, and adipic acid; inorganic acids such as hydrochloric acid, sulfuric acid, nitric acid, phosphoric acid, boric acid, and partial salts of polybasic acids, e.g., $KH_2PO_4$, $NaHSO_4$; group Ia or IIa metal hydroxides such as sodium hydroxide, and potassium hydroxide; ammonia; oxidizing agents such as hydrogen peroxide, benzoyl peroxide, ammonium persulfate, potassium permagnate, sodium bicarbonate, hypochloric salts, and the like; and mixtures thereof. Preferred chemical agents of the present invention include ammonium persulfate, sulfuric acid, hydrochloric acid, and mixtures thereof.

Chemical modifications may also include derivatization of starch by reaction of its OH groups with alkylene oxides, and other ether-, ester-, urethane-, carbamate-, or isocyanate-forming substances. Hydroxyalkyl, acetyl, or carbamate starches or mixtures thereof are preferred chemically modified starches. The degree of substitution of the chemically modified starch is 0.05 to 3.0, preferably 0.05 to 0.2.

Biological modifications of starch include bacterial digestion of the carbohydrate bonds, or enzymatic hydrolysis using enzymes such as amylase, amylopectase, and the like.

The starch typically has a bound water content of about 5% to 16% by weight of starch. A water content of about 8% to about 12% by weight of starch is most typical. In one embodiment of the invention, the amylose content of the starch is typically from 0% to about 80%, more typically from about 20% to about 35%, by weight of starch.

Natural, unmodified starch generally has a very high average molecular weight and a broad molecular weight distribution (e.g. natural corn starch has an average molecular weight of about 10,000,000 and a molecular weight distribution greater than 1000, where molecular weight distribution is the weight average molecular weight divided by the number average molecular weight). The average molecular weight of starch can be reduced to the desirable range for the present invention by chain scission (oxidative or enzymatic), hydrolysis (acid or alkaline catalyzed), physical/mechanical degradation (e.g., via the thermomechanical energy input of the processing equipment), or combinations thereof. These reactions also reduce the molecular weight distribution of starch to less than about 600, typically to less than about 300. The thermomechanical method and the oxidation method offer an additional advantage in that they are capable of being carried out in situ during the melt spinning process.

In one embodiment, the natural starch is hydrolyzed in the presence of acid, such as hydrochloric acid or sulfuric acid, to reduce the molecular weight and molecular weight distribution. In another embodiment, a chain scission agent may be incorporated into the melt spinnable starch composition such that the chain scission reaction takes place substantially concurrently with the blending of the starch with other components. Nonlimiting examples of oxidative chain scission agents suitable for use herein include ammonium persulfate, hydrogen peroxide, hypochlorate salts, potassium permanganate, and mixtures thereof. Typically, the chain scission agent is added in an amount effective to reduce the weight-average molecular weight of the starch to the desirable range. For example, it is found that for uniaxial or biaxial melt attenuation processes, the starch should have a weight-average molecular weight ranging from about 1,000 to about 2,000,000, more typically from about 1,500 to about 800,000, most typically from about 2,000 to about 500,000. It is found that compositions having modified starch in the above molecular weight range have a suitable melt shear viscosity, and thus improved melt processability. The improved melt processability is evident in less interruptions of the process (e.g., reduced breakage, shots, defects, hang-ups) and better surface appearance and strength properties of the product.

In some embodiments of the present invention, the composition herein comprises from about 5% to about 99.99%, typically 20 to about 95 wt %, more typically from about 30 to about 95 wt %, even more typically from about 50 to about 85 wt %, even more typically from 40% to 70%, and most typically from about 45% to about 65% of starch. In some embodiments of the present invention (for example when the processing temperature is high ((e.g., >80° C.), starch levels of 70% to 95% may desirably be employed). Because water bound in the starch cannot be distinguished from unbound water added to the starch composition as the polar solvent or plasticizer, when the weight of the starch in the composition is being discussed, bound water shall not be included in the weight of the starch as a percent of the composition.

B. High Polymers

High molecular weight polymers (hereinafter "high polymers") which are substantially compatible with starch can also be useful in order to achieve the desired extensional viscosity characteristics for the starch compositions herein. In one embodiment, the high polymer preferably has a substantially linear chain structure, though a linear chain having short (C1–C3) branches or a branched chain having one to three long branches are also suitable for use herein. As used herein, the term "substantially compatible" means when heated to a temperature above the softening and/or the melting temperature of the composition, the high polymer is capable of forming a substantially homogeneous mixture with the starch (i.e., the composition appears transparent or translucent to the naked eye).

The Hildebrand solubility parameter ($\delta$) can be used to estimate the compatibility between starch and the polymer. Generally, substantial compatibility between two materials can be expected when their solubility parameters are similar. It is known that water has a $\delta_{water}$ value of 48.0 $MPa^{1/2}$, which is the highest among common solvents, probably due to the strong hydrogen bonding capacity of water. It is believed that starch typically has a $\delta_{starch}$ value similar to that of cellulose (about 34 $MPa^{1/2}$).

Without being bound by theory, it is believed that polymers suitable for use herein preferably interact with the starch molecules on the molecular level in order to form a substantially compatible mixture. The interactions range from the strong, chemical type interactions such as hydrogen bonding between polymer and starch, to merely physical entanglements between them. The polymers useful herein are preferably high molecular weight, substantially linear chain molecules. The highly branched structure of an amylopectin molecule favors the branches to interact intramolecularly, due to the proximity of the branches within a single molecule. The compatibility with starch enables suitable polymers to be intimately mixed and chemically interact and/or physically entangle with the branched amylopectin molecules such that the amylopectin molecules associate with one another via the polymers. The high molecular weight of the polymer enables it to simultaneously interact/entangle with several starch molecules. That is, the high polymers can function as molecular links for starch molecules. The linking function of the high polymers can be particularly important for starches high in amylopectin content. The entanglements and/or associations between starch and polymers enhance the melt extensibility of the starch composition such that the composition is suitable for extensional processes. In one embodiment, it is found that the composition can be melt attenuated uniaxially to a very high draw ratio (greater than 1000).

In order to effectively form entanglements and/or associations with the starch molecules, the high polymer suitable for use herein should have a weight-average molecular weight of at least 500,000. Typically the weight average molecular weight of the polymer ranges from about 500,000 to about 25,000,000, more typically from about 800,000 to about 22,000,000, even more typically from about 1,000,000 to about 20,000,000, and most typically from about 2,000,000 to about 15,000,000. The high molecular weight polymers are preferred in some embodiments of the invention due to the ability to simultaneously interact with several starch molecules, thereby increasing extensional melt viscosity and reducing melt fracture.

Suitable high polymers have a $\delta_{polymer}$ such that the difference between $\delta_{starch}$ and $\delta_{polymer}$ is less than about 10 $MPa^{1/2}$, preferably less than about 5 $MPa^{1/2}$, and more preferably less than about 3 $MPa^{1/2}$. Nonlimiting examples of suitable high polymers include polyacrylamide and derivatives such as carboxyl modified polyacrylamide; acrylic polymers and copolymers including polyacrylic acid, polymethacrylic acid, and their partial esters; vinyl polymers including polyvinyl alcohol, polyvinylacetate, polyvinylpyrrolidone, polyethylene vinyl acetate, polyethyleneimine, and the like; polyamides; polyalkylene oxides such as polyethylene oxide, polypropylene oxide, polyethylenepropylene oxide, and mixtures thereof. Copolymers made from mixtures of monomers selected from any of the aforementioned polymers are also suitable herein. Other exemplary high polymers include water soluble polysaccharides such as alginates, carrageenans, pectin and derivatives, chitin and derivatives, and the like; gums such as guar gum, xanthum gum, agar, gum arabic, karaya gum, tragacanth gum, locust bean gum, and like gums; water soluble derivatives of cellulose, such as alkylcellulose, hydroxyalkylcellulose, carboxyalkylcellulose, and the like; and mixtures thereof.

Some polymers (e.g., polyacrylic acid, polymethacrylic acid) are generally not available in the high molecular weight range (i.e., 500,000 or higher). A small amount of crosslinking agents may be added to create branched polymers of suitably high molecular weight useful herein.

The high polymer, when used in a melt blowing process, is added to the composition of the present invention in an amount effective to visibly reduce the melt fracture and capillary breakage of fibers during the spinning process such that substantially continuous fibers having relatively consistent diameter can be melt spun. Regardless of the process employed to produce starch fibers, filaments, films or foams, these polymers, when used, are typically present in the range from about 0.001 to about 10 wt %, more typically from about 0.005 to about 5 wt %, even more typically from about 0.01 to about 1 wt %, and most typically from about 0.05 to about 0.5 wt % of the composition. It is surprising to find that at a relatively low concentration, these polymers can significantly improve the melt extensibility of the starch composition.

C. Additives

The starch compositions may optionally include additives to enhance melt flow and melt processability, particularly the extensibility of the composition under the melt processing conditions. The additives may function as plasticizers and/or diluents to reduce the melt shear viscosity of the starch composition. In one embodiment of the present invention, additives are typically employed at levels ranging from about 0.001% to about 95%, more typically from about 5% to about 80%, even more typically from about 5% to about 70%, even more typically from about 15% to about 50%, even more typically from about 30% to about 60% and most typically from about 35% to about 55%. In another embodiment of the present invention (for example when high die temperatures are employed), additives can preferably be incorporated into the compositions at levels ranging from abut 5% to about 30%.

1. Plasticizers

The plasticizers, when used, may be added to the composition of the present invention in an amount effective to improve the flow, hence, the melt processability. The plasticizers may also improve the flexibility of the final products, which is believed to be due to the lowering of the glass transition temperature of the composition by the plasticizer. The plasticizers should preferably be substantially compatible with the polymeric components of the present invention so that the plasticizers may effectively modify the properties of the composition. As used herein, the term "substantially compatible" means when heated to a temperature above the softening and/or the melting temperature of the composition, the plasticizer is capable of forming a substantially homogeneous mixture with starch (i.e., the composition appears transparent or translucent to the naked eye).

Suitable for use herein as hydroxyl plasticizers are organic compounds having at least one hydroxyl group, preferably a polyol. Without being bound by theory, it is believed that the hydroxyl groups of the plasticizers enhance compatibility by forming hydrogen bonds with the starch matrix material. Nonlimiting examples of useful hydroxyl plasticizers include sugars such as glucose, sucrose, fructose, raffinose, maltodextrose, galactose, xylose, maltose, lactose, mannose, erythrose, glycerol, and pentaerythritol; sugar alcohols such as erythritol, xylitol, maltitol, mannitol and sorbitol; polyols such as ethylene glycol, propylene glycol, dipropylene glycol, butylene glycol, hexane triol, and the like, and polymers thereof; and mixtures thereof.

Also useful herein as hydroxyl plasticizers are poloxomers (polyoxyethylene/polyoxypropylene block copolymers) and poloxamines (polyoxyethylene/polyoxypropylene block copolymers of ethylene diamine). Suitable "poloxomers" comprise block copolymers of polyoxyethylene/polyoxypropylene having the following structure:

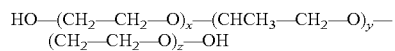

wherein x has a value ranging from about 2 to about 40, y has a value ranging from about 10 to about 50, and z has a value ranging from about 2 to about 40, and preferably x and z have the same value. These copolymers are available as Pluronic® from BASF Corp., Parsippany, N.J. Suitable poloxomers and poloxamines are available as Synperonic® from ICI Chemicals, Wilmington, Del., or as Tetronic® from BASF Corp., Parsippany, N.J.

Also suitable for use herein as hydroxyl-free plasticizers are other hydrogen bond forming organic compounds which do not have hydroxyl group, including urea and urea derivatives; anhydrides of sugar alcohols such as sorbitan; animal proteins such as gelatin; vegetable proteins such as sunflower protein, soybean protein, and cotton seed protein; and mixtures thereof. All of the plasticizers may be used alone or in mixtures thereof.

Typically, the hydroxyl plasticizer comprises from about 1 wt % to about 70 wt %, more typically from about 2 wt % to about 60 wt %, most typically from about 3 wt % to about 40 wt % of the starch composition. The hydroxyl-free plasticizer typically comprises from about 0.1 wt % to about 70 wt %, more typically from about 2 wt % to about 50 wt %, most typically from about 3 wt % to about 40 wt % of the starch composition.

In one embodiment, a mixture of the hydroxyl and hydroxyl-free plasticizers is used, wherein the hydroxyl plasticizers are sugars, such as sucrose, fructose, and sorbitol, and the hydroxyl-free plasticizers are urea and urea derivatives. It is found that urea and its derivatives in the starch composition of the present invention have a strong tendency to crystallize, that is, crystallization of urea and its derivatives occurs even under fast cooling condition such as melt blowing, spun bonding, melt extrusion, wet spinning, and the like. Therefore, urea and urea derivatives may be used as solidifying agents for modifying or controlling the solidification rate of the starch composition of the present invention. In a preferred embodiment, a mixture of sucrose and urea is added to the starch/polymer composition in an amount effective to achieve the desired melt processability and solidification rate.

2. Diluents

Materials that function as diluents, such as polar solvents, may optionally be added to the starch compositions of the present invention to adjust the melt shear viscosity and enhance the melt spinnability of the starch compositions. Generally, the melt shear viscosity decreases in a nonlinear manner as the diluent content is increased. Typically, the diluent is added in an amount from about 5 wt % to about 60 wt %, more typically from about 7 wt % to about 50 wt %, most typically from about 10 wt % to about 30 wt %, of the total composition.

Examples of materials that may function as diluents are polar solvents having a solubility parameter δ ranging from about 28 to about 48 MPa$^{1/2}$. Nonlimiting examples include water, C1–C18 linear or branched alcohols, DMSO (dimethyl sulphoxide), formamide and derivatives such as N-methyl formamide, N-ethyl formamide, acetamide and derivatives such as methyl acetamide, Cellosolv® (a glycol alkyl ether) and derivatives, such as butyl Cellosolv®, benzyl Cellosolv®, Cellosolv® acetate (all Cellosolv® and derivatives are available from J. T. Baker, Phillipsburg, N.J.), hydrazine, and ammonia. It is also known that the δ value of a solvent mixture can be determined by volume-averaging the δ values of the individual solvents. Therefore, mixed solvents having δ values within the above-identified range (i.e., from about 19 to about 48 MPa$^{1/2}$) are also suitable for use herein. For example, a mixed solvent of DMSO/water having a composition of 90/10 v/v would have a δ value of about 31.5; such a mixed solvent system is suitable for use herein.

It is found that polar solvents capable of forming hydrogen bonding may be more effective in lowering the melt viscosity of the composition. As such, a lower amount of the polar solvent is sufficient to adjust the viscosity to the desired range for melt spinning. Using a lower amount of the polar solvent provides a further advantage of reducing the need for an evaporation step during or subsequent to the melt processing step, which results in operating cost advantages such as lower energy consumption and lower solvent recovery costs, as well as lower costs for environmental/regulatory compliance.

The starch composition may optionally include liquid or volatile processing aids which function mainly as viscosity modifiers of the melt compositions. The processing aid is substantially volatized and removed during the melt processing stage such that only a residual/trace amount remains in the final product. Thus, they do not adversely affect the strength, modulus or other properties of the final product. The polar solvents disclosed above may also function as volatile processing aids. Other nonlimiting examples include carbonates such as sodium bicarbonate.

D. Other Optional Ingredients

Optionally, other ingredients may be incorporated into the spinnable starch composition to modify the processability and/or to modify physical properties such as elasticity, tensile strength and modulus of the final product. Nonlimiting examples include oxidation agents, cross-linking agents, emulsifiers, surfactants, debonding agents, lubricants, other processing aids, optical brighteners, antioxidants, flame retardants, dyes, pigments, fillers, proteins and their alkali salts, biodegradable synthetic polymers, waxes, low melting synthetic thermoplastic polymers, tackifying resins, extenders, wet strength resins and mixtures thereof. These optional ingredients may be present in quantities ranging from about 0.1% to about 70%, typically from about 1% to about 60%, more typically from about 5% to about 50%, and most typically from about 10% to about 50%, by weight of the composition.

Exemplary biodegradable synthetic polymers include polycaprolactone; polyhydroxyalkanoates including polyhydroxybutyrates, and polyhydroxyvalerates; polylactides; and mixtures thereof.

Lubricant compounds may further be added to improve the flow properties of the starch material during the processes used for producing the present invention. The lubricant compounds can include animal or vegetable fats, preferably in their hydrogenated form, especially those which are solid at room temperature. Additional lubricant materials include mono-glycerides and di-glycerides and phosphatides, especially lecithin. For the present invention, a preferred lubricant compound includes the mono-glyceride, glycerol mono-stearate.

Further additives including inorganic particles such as the oxides of magnesium, aluminum, silicon, and titanium may be added as inexpensive fillers or extenders. Additionally, additives such as inorganic salts, including alkali metal salts, alkaline earth metal salts, phosphate salts, etc., may be used.

Other additives may be desirable depending upon the particular end use of the product contemplated. For example, in products such as toilet tissue, disposable towels, facial tissues and other similar products, wet strength is a desirable attribute. Thus, it is often desirable to add to the starch polymer cross-linking agents known in the art as "wet strength" resins.

A general dissertation on the types of wet strength resins utilized in the paper art can be found in TAPPI monograph series No. 29, Wet Strength in Paper and Paperboard, Technical Association of the Pulp and Paper Industry (New York, 1965). The most useful wet strength resins have generally been cationic in character. Polyamide-epichlorohydrin resins are cationic polyamide amine-epichlorohydrin wet strength resins which have been found to be of particular utility. Suitable types of such resins are described in U.S. Pat. No. 3,700,623, issued on Oct. 24, 1972, and U.S. Pat. No. 3,772,076, issued on Nov. 13, 1973, both issued to Keim and both being hereby incorporated by reference. One commercial source of a useful polyamide-epichlorohydrin resin is Hercules, Inc. of Wilmington, Del., which markets such resins under the mark Kymene®.

Glyoxylated polyacrylamide resins have also been found to be of utility as wet strength resins. These resins are described in U.S. Pat. No. 3,556,932, issued on Jan. 19, 1971, to Coscia, et al. and U.S. Pat. No. 3,556,933, issued on Jan. 19, 1971, to Williams et al., both patents being incorporated herein by reference. One commercial source of glyoxylated polyacrylamide resins is Cytec Co. of Stanford, Conn., which markets one such resin under the mark Parez® 631 NC.

It is found that when suitable cross-linking agent such as Parez® 631NC is added to the starch composition of the present invention under acidic condition, the composition is rendered water insoluble. That is, the water solubility of the composition, as tested by the Test Method described hereinafter, is less than 30%, typically less than 20%, more typically less than 10% and most typically less than 5%. The products such as fibers, filaments and films made from such a composition are also water insoluble.

Still other water-soluble cationic resins finding utility in this invention are urea formaldehyde and melamine formaldehyde resins. The more common functional groups of these polyfunctional resins are nitrogen containing groups such as amino groups and methylol groups attached to nitrogen. Polyethylenimine type resins may also find utility in the present invention. In addition, temporary wet strength resins such as Caldas® 10 (manufactured by Japan Carlit) and CoBond® 1000 (manufactured by National Starch and Chemical Company) may be used in the present invention.

For the present invention, a suitable cross-linking agent is added to the composition in quantities ranging from about 0.1% by weight to about 10% by weight, more typically from about 0.1% by weight to about 3% by weight.

II. The Rheology of the Starch Compositions

In order to produce fibers, filaments, films or foams via conventional thermoplastic processing, the starch compositions herein should desirably exhibit certain rheological behavior during processing, including a certain range of extensional viscosities and a certain range of capillary numbers.

As used herein a "starch filament" is a slender, thin, and highly flexible object comprising starch and having a major axis which is very long, compared to the fiber's two mutually-orthogonal axes that are perpendicular to the major axis. An aspect ratio of the major axis's length to an equivalent diameter (hereinafter defined) of the filaments's cross section perpendicular to the major axis is greater than 100/1, more specifically greater than 500/1 and still more specifically greater than 5000/1. The starch filaments may comprise other matter, such as, for example water, plasticizers and other optional additives.

Extensional or elongational viscosity ($\eta_e$) relates to melt extensibility of the composition, and is particularly important for extensional processes such as fiber, filament, film or foam making. The extensional viscosity includes three types of deformation: uniaxial or simple extensional viscosity, biaxial extensional viscosity, and pure shear extensional viscosity. The uniaxial extensional viscosity is important for uniaxial extensional processes such as fiber spinning, melt blowing, and spun bonding. The other two extensional viscosities are important for the biaxial extension or forming processes for making films, filaments, foams, sheets or parts.

For conventional fiber spinning thermoplastics such as polyolefins, polyamides and polyesters, there is a strong correlation between extensional viscosity and shear viscosity of these conventional thermoplastic materials and blends thereof. That is, the spinnability of the material can be determined simply by the melt shear viscosity, even though the spinnablity is a property controlled primarily by melt extensional viscosity. The correlation is quite robust such that the fiber industry has relied on the melt shear viscosity in selecting and formulating melt spinnable materials. The melt extensional viscosity has rarely been used as an industrial screening tool.

It is therefore surprising to find that the starch compositions of the present invention do not necessarily exhibit such a correlation between shear and extensional viscosities. The starch compositions herein exhibit melt flow behavior typical of a non-Newtonian fluid and as such may exhibit a strain hardening behavior, that is, the extensional viscosity increases as the strain or deformation increases.

For example, when a high polymer selected according to the present invention is added to a starch composition, the shear viscosity of the composition remains relatively unchanged, or even decreases slightly. Based on conventional wisdom, such a starch composition would exhibit decreased melt processability and would not be suitable for melt extensional processes. However, it is surprisingly found that the starch composition herein shows a significant increase in extensional viscosity when even a small amount of high polymer is added. Consequently, the starch composition herein is found to have enhanced melt extensibility and is suitable for melt extensional processes (e.g., blow molding, spun bonding, blown film molding, foam molding, and the like).

A starch composition having a shear viscosity, measured according to the Test Method disclosed hereinafter, of less than about 30 Pa·s, typically from about 0.1 to about 10 Pa·s, more typically from about 1 to about 8 Pa·s, is useful in the melt attenuation processes herein. Some starch compositions herein may have low melt viscosity such that they may be mixed, conveyed, or otherwise processed in traditional polymer processing equipment typically used for viscous fluids, such as a stationary mixer equipped with metering pump and spinneret. The shear viscosity of the starch composition may be effectively modified by the molecular weight and molecular weight distribution of the starch, the molecular weight of the high polymer, and the amount of plasticizers and/or solvents used. It is found that reducing the average molecular weight of the starch is an effective way to lower the shear viscosity of the composition.

In one embodiment of the present invention, the melt-processable starch compositions of the present invention further have an extensional viscosity in the range of from about 50 pascal•seconds to about 20,000 pascal•seconds, typically from about 100 pascal•seconds to about 15,000 pascal•seconds, more typically from about 200 pascal•seconds to about 10,000 pascal•seconds, even more typically from about 300 pascal•seconds to about 5000 pascal•seconds and most typically from about 500 pascal•seconds to about 3500 pascal•seconds at the die temperature. The extensional viscosity is calculated according to the method set forth hereinafter in the Analytical Methods section.

Many factors can affect the rheological behavior of the starch composition (including the extensional viscosity), including the amount and the type of polymeric components used, the molecular weight and molecular weight distribution of the components (including the starch and the high polymers), the amylose content of the starch, the amount and type of additives (e.g., plasticizers, diluents, processing aids), the processing conditions such as temperature, pressure, rate of deformation, and relative humidity, and in the case of non-Newtonian materials, the deformation history (i.e., a time or strain history dependence).

In one preferred embodiment of the present invention, it is found that the presence and properties of high polymers have a significant effect on melt extensional viscosity. The high polymers useful for enhancing the melt extensibility of the starch composition of the present invention are typically high molecular weight, substantially linear polymers. Moreover, high polymers that are substantially compatible with starch are most effective in enhancing the melt extensibility of the starch composition.

It has been found that starch compositions useful for melt extensional processes typically have their extensional viscosity increased by a factor of at least 10 when a selected high polymer is added to the composition. Typically, the starch compositions of present invention show an increase in the extensional viscosity of a factor of about 10 to about 500, more typically of about 20 to about 300, and most typically from about 30 to about 100, when a selected high polymer is added. The higher the level of the high polymer, the greater the increase in extensional viscosity.

The type and level of starch that is employed can also have an impact on the extensional viscosity of the starch composition. In general, as the amylose content of the starch decreases, the extensional viscosity increases. Also, in general, as the molecular weight of the starch within the prescribed range increases, the extensional viscosity increases. Lastly, in general, as the level of starch in the compositions increases, the extensional viscosity increases. (Conversely, in general, as the level of additive in the compositions increases, the extensional viscosity decreases).

The Trouton ratio (Tr) is often used to express the extensional flow behavior. The Trouton ratio is defined as the ratio between the extensional viscosity ($\eta_e$) and the shear viscosity ($\eta_s$), $$Tr = \eta_e(\dot{\epsilon}, t)/\eta_s$$

wherein the extensional viscosity $\eta_e$ is dependent on the deformation rate ($\dot{\epsilon}$) and time (t). For a Newtonian fluid, the uniaxial extension Trouton ratio has a constant value of 3. For a non-Newtonian fluid, such as the starch compositions herein, the extensional viscosity is dependent on the deformation rate ($\dot{\epsilon}$) and time (t). It has also been found that melt processable compositions of the present invention typically have a Trouton ratio of at least about 3. Typically, the Trouton ratio ranges from about 10 to about 5,000, more typically from about 20 to about 1,000, even more typically from about 30 to about 500, when measured at the processing temperature and 700 s$^{-1}$. As used herein "Processing Temperature" means the temperature of the starch composition, at which temperature the starch fibers, filaments, films or foams of the present invention are formed, for example, by attenuation.

Applicants have also found that the Capillary Number (Ca) of the starch composition as it passes through the die is important for melt processability. The Capillary Number is a dimensionless number representing the ratio of the viscous fluid forces to surface tension forces. Near the exit of a capillary die, if the viscous forces are not significantly larger than the surface tension forces, the fluid filament will break into droplets, which is commonly termed atomization. The Capillary Number is calculated according to the following equation:

$$Ca=(\eta_s \cdot Q)/(\pi \cdot r^2 \cdot \sigma)$$

where $\eta_s$ is the shear viscosity in pascal seconds measured at a shear rate of 3000 s$^{-1}$, Q is the volumetric fluid flow rate through the capillary die in m$^3$/s, r is the radius of the capillary die in meters (for non-circular orifices, the euqivalent diamter/radius can be used) and $\sigma$ is the surface tension of the fluid in Newtons per meter.

Because the Capillary Number is related to shear viscosity as described above, it is influenced by the same factors that affect shear viscosity (hereinbefore described) and in the same way.

In one embodiment of the present invention, the melt-processable starch compositions herein have a capillary number as they pass through the die of at least about 1, typically in the range of from 1 to 100, more typically in the range of from about 3 to about 50, most typically in the range of from about 5 to about 30.

III. Processes for Preparing Starch Fibers, Films or Foams of the Present Invention The starch composition herein is processed in a flowable state, which typically occurs at a temperature at least equal to or higher than its "melting temperature". Therefore, the processing temperature range is controlled by the "melting temperature" of the starch composition, which is measured according to the Test Method described in detail herein. Processing temperatures typically range from about 20 to 180° C., more specifically from about 20 to about 90° C., and most specifically from about 50 to about 80° C.

It is to be understood that some starch compositions are pseudo-thermoplastic compositions and as such may not exhibit pure "melting" behavior. As used herein, "Pseudo-thermoplastic composition" is intended to denote materials which by the influence of elevated temperatures may be softened to such a degree that they can be brought into a flowable state, and in this condition may be shaped as desired. Pseudo-thermoplastic materials may be formed under simultaneous influence of heat and pressure. Pseudo-thermoplastic compositions differ from thermoplastic compositions in that the softening or liquifying of the pseudo-thermoplastic is caused by softeners or solvents present without which it would be impossible to bring them by any temperature or pressure into a soft or flowable condition necessary for shaping since pseudo thermoplastics do not melt as such.

As used herein, the term "melting temperature" means the temperature or the range of temperature at or above which the composition melts or softens. The melting temperature of the starch composition herein ranges from about 20 to 180° C., more specifically from about 20 to about 90° C., and most specifically from about 50 to about 80° C. In general, the higher the level of starch solids present in the starch composition, the higher the melting temperature of the starch composition within this range, and thus, the higher the processing temperature. When a die is used to process the starch compositions herein into fibers, filaments, films or foams, the die temperature is kept above the melting temperature of the starch composition. In general, as the die temperature increases, the extensional viscosity of the starch composition decreases.

Exemplary uniaxial extensional processes suitable for the starch compositions include melt spinning, melt blowing, and spun bonding. These processes are described in detail in U.S. Pat. No. 4,064,605, issued on Dec. 27, 1977 to Akiyama et al.; U.S. Pat. No. 4,418,026, issued on Nov. 29, 1983 to Blackie et al.; U.S. Pat. No. 4,855,179, issued on Aug. 8, 1989 to Bourland et al.; U.S. Pat. No. 4,909,976, issued on Mar. 20, 1990 to Cuculo et al.; U.S. Pat. No. 5,145,631, issued on Sep. 8, 1992 to Jezic; U.S. Pat. No. 5,516,815, issued on May 14, 1996 to Buehler et al.; and U.S. Pat. No. 5,342,335, issued on Aug. 30, 1994 to Rhim et al.; the disclosure of all of the above are incorporated herein by reference.

The rheological behavior of the present starch compositions also makes it suitable for use in electrostatic processes. Starch fibers and filaments can be produced by an electro-spinning process, wherein an electric field is applied to a starch solution to form a charged starch jets. The electro-spinning process is well known in the art. The dissertation entitled "The Electro-Spinning Process and Applications of Electro-Spun Fibers" by Doshi, Jayesh, Natwarlal, Ph.D., 1994, describes an electro-spinning process and conducts a study of the forces involved in the process. This dissertation also explores some commercial applications of the electro-spun filaments. This dissertation is incorporated herein by reference for the purposes of describing the principles of the electro-spinning processes.

U.S. Pat. No. 1,975,504 (Oct. 2, 1934); U.S. Pat. No. 2,123,992 (Jul. 19, 1938); U.S. Pat. No. 2,116,942 (May 10, 1938); U.S. Pat. No. 2,109,333 (Feb. 22, 1938); U.S. Pat. No. 2,160,962 (Jun. 6, 1939); U.S. Pat. No. 2,187,306 (Jan. 16, 1940); and U.S. Pat. No. 2,158,416 (May 16, 1939), all issued to Formhals, describe electro-spinning processes and equipment therefor. Other references describing electro-spinning processes include: U.S. Pat. No. 3,280,229 (Oct. 18, 1966) issued to Simons; U.S. Pat. No. 4,044,404 (Aug. 30, 1977) issued to Martin et al.; U.S. Pat. No. 4,069,026 (Jan. 17, 1978) issued to Simm et al.; U.S. Pat. No. 4,143, 196 (Mar. 6, 1979) issued to Simm; U.S. Pat. No. 4,223,101 (Sep. 16, 1980) issued to Fine et al.; U.S. Pat. No. 4,230,650 (Oct. 28, 1980) issued to Guignard; U.S. Pat. No. 4,232,525 (Nov. 11, 1980) issued to Enjo et al.; U.S. Pat. No. 4,287,139 (Sep. 1, 1981) issued to Guignard; U.S. Pat. No. 4,323,525 (Apr. 6, 1982) issued to Bornat; U.S. Pat. No. 4,552,707 (Nov. 12, 1985) issued to How; U.S. Pat. No. 4,689,186 (Aug. 25, 1987) issued to Bornat; U.S. Pat. No. 4,798,607 (Jan. 17, 1989) issued to Middleton et al.; U.S. Pat. No.

4,904,272 (Feb. 27, 1990) issued to Middleton et al.; U.S. Pat. No. 4,968,238 (Nov. 6, 1990) issued to Satterfield et al.; U.S. Pat. No. 5,024,789 (Jan. 18, 1991) issued to Barry; U.S. Pat. No. 6,106,913 (Aug. 22, 2000) issued to Scardino et al.; and, U.S. Pat. No. 6,110,590 (Aug. 29, 2000) issued to Zarkoob et al. The disclosures of the foregoing patents are incorporated herein by reference for the limited purpose of describing the general principles of electro-spinning processes and equipment therefor.

The resultant fibers or filaments prepared by any of the aforementioned processes may find use in filters for air, oil and water; vacuum cleaner filters; furnace filters; face masks; coffee filters, tea or coffee bags; thermal insulation materials and sound insulation materials; nonwovens for one-time use sanitary products such as diapers, feminine pads, and incontinence articles; biodegradable textile fabrics for improved moisture absorption and softness of wear such as microfiber or breathable fabrics; an electrostatically charged, structured web for collecting and removing dust; reinforcements and webs for hard grades of paper, such as wrapping paper, writing paper, newsprint, corrugated paper board, and webs for tissue grades of paper such as toilet paper, paper towel, napkins and facial tissue; medical uses such as surgical drapes, wound dressing, bandages, dermal patches and self-dissolving sutures; and dental uses such as dental floss and toothbrush bristles. The fibrous web may also include odor absorbents, termite repellents, insecticides, rodenticides, and the like, for specific uses. The resultant product absorbs water and oil and may find use in oil or water spill clean-up, or controlled water retention and release for agricultural or horticultural applications. The resultant starch fibers or fiber webs may also be incorporated into other materials such as saw dust, wood pulp, plastics, and concrete, to form composite materials, which can be used as building materials such as walls, support beams, pressed boards, dry walls and backings, and ceiling tiles; other medical uses such as casts, splints, and tongue depressors; and in fireplace logs for decorative and/or burning purpose.

The melt rheological behavior of the present starch composition also makes it suitable for use in conventional thermoplastic processes that involves biaxial extension of the material. By having the proper melt shear viscosity and biaxial extensional viscosity, the starch compositions of the present invention may substantially reduce the occurrence of tearing, surface defects, and other breakdowns or defects that interrupt continuous processes and produce unsatisfactory products. These processes include blow molding, blown film extrusion or coextrusion, vacuum forming, pressure forming, compression molding, transfer molding and injection molding. Nonlimiting examples of these processes are described in details in U.S. Pat. No. 5,405,564, issued on Apr. 11, 1995 to Stepto et al.; U.S. Pat. No. 5,468,444, issued on Nov. 21, 1995 to Yazaki et al.; U.S. Pat. No. 5,462,982, issued on Oct. 31, 1995 to Bastioli et al.; the disclosure of all of the above are hereby incorporated by reference. The articles produced by these processes include sheets, films, coatings, laminates, pipes, rods, bags, and shaped articles (such as bottles, containers). The articles may find use as bags such as shopping bags, grocery bags, and garbage bags; pouches for food storage or cooking; microwavable containers for frozen food; and pharmaceutical uses such as capsules or coatings for medicine. The films may be substantially transparent for use as food wraps, shrink wraps or windowed envelopes. The films may also be further processed for use as an inexpensive, biodegradable carrier for other materials such as seeds or fertilizers. Adhesives may be applied to the films or sheets for other uses such as labels.

The starch compositions of the present invention may also be made into a foamed structure by controlled removal of the volatile components (e.g., water, polar solvents). However, foaming or expanding agents are generally incorporated to produce articles having foamed or porous internal structure. Exemplary foaming or expanding agents include carbon dioxide, n-pentane, and carbonate salts such as sodium bicarbonate, either alone or in combination with a polymeric acid which has lateral carboxyl groups (e.g., polyacrylic acid, ethylene-acrylic copolymer). Nonlimiting examples of the foaming and forming processes are described in U.S. Pat. No. 5,288,765, issued on Feb. 22, 1994 to Bastioli et al.; U.S. Pat. No. 5,496,895, issued on Mar. 5, 1996 to Chinnaswamy et al.; U.S. Pat. No. 5,705,536, issued on Jan. 6, 1998 to Tomka; and U.S. Pat. No. 5,736,586, issued on Apr. 7, 1998 to Bastioli et al.; the disclosures of which are hereby incorporated by reference. The resultant products may find use in egg cartons; foamed cups for hot beverages; containers for fast food; meat trays; plates and bowls for one-time use such as at picnic or parties; packaging materials, either loose-fill or molded to conform to the packed article (e.g., a computer shipping package); thermal insulation materials; and noise insulation or sound proofing materials.

IV. Characteristics of the Fibers, Films and Foams of the Present Invention

When the starch composition of the present composition is subjected to an uniaxial extensional process, a draw ratio, expressed in $(D_O^2/D^2)$ wherein $D_O$ is the equivalent diameter of filament before drawing and D is the equivalent diameter of the drawn fiber, greater than 1000 can be easily achieved. The starch composition of the present invention typically achieves a draw ratio from about 100 to about 10,000, more typically greater than about 1,000, even more typically greater than about 3,000 and most typically greater than about 5,000. More specifically, the starch composition of the present invention has sufficient melt extensibility to be melt drawn to fine fibers or filaments having a finite average equivalent diameter of less than 10 microns, and most specifically less than 5 microns.

As used herein "equivalent diameter" is used to define a cross-sectional area and a surface area of an individual starch fiber or filament, without regard to the shape of the cross sectional area. Thus, the equivalent diameter is a parameter that satisfies the equation $S=\frac{1}{4}\pi D^2$, where S is the starch fiber or filament's cross-sectional area (without regard to its geometrical shape), $\pi=3.14159$, and D is the equivalent diameter. For example, the cross-section having a rectangular shape formed by two mutually opposite sides "A" and two mutually opposite sides "B" can be expressed as: $S=A\times B$. At the same time, this cross-sectional area can be expressed as a circular area having the equivalent diameter D. Then, the equivalent diameter D can be calculated from the formula: $S=\frac{1}{4}\pi D^2$, where S is the known area of the rectangle. (Of course, the equivalent diameter of a circle is the circle's real diameter.)

"Decitex" or "dtex" is a unit of measure for a starch fiber expressed in grams per 10,000 meters. According to the present invention, the starch fibers can have a size ranging from about 0.01 decitex to about 135 decitex, more specifically from about 0.02 decitex to about 5 decitex. Starch fibers can have various cross sectional shapes, including, but not limited to, circular, oval, rectangular, triangular, hexagonal, cross-like, star-like, irregular and any combinations thereof. One skilled in the art will understand that such a variety of shapes can be formed by different shapes of die nozzles used to produce starch fibers.

When the starch composition of the present invention is subjected to a biaxial extensional process, the enhanced melt extensibility of the composition allows it to be melt drawn to films having a finite average caliper of less than 0.8 mils, typically less than 0.6 mils, more typically less than 0.4 mils, even more typically less than 0.2 mils, and most typically less than 0.1 mils.

Test Methods

A. Shear Viscosity

The shear viscosity of the composition is measured using a capillary rheometer (Model Rheograph 2003, manufactured by Goettfert). The measurements are conducted using a capillary die having a diameter D of 1.0 mm and a length L of 30 mm (i.e., L/D=30). The die is attached to the lower end of a barrel, which is held at a test temperature (t) ranging from 25° C. to 90° C. A sample composition which has been preheated to the test temperature is loaded into the barrel section of the rheometer, and substantially fills the barrel section (about 60 grams of sample is used). The barrel is held at the specified test temperature (t). If after the loading, air bubbles to the surface, compaction prior to running the test is used to rid the sample of entrapped air. A piston is programmed to push the sample from the barrel through the capillary die at a set of chosen rates. As the sample goes from the barrel through the capillary die, the sample experiences a pressure drop. An apparent shear viscosity is calculated from the pressure drop and the flow rate of the sample through the capillary die. Then log (apparent shear viscosity) is plotted against log (shear rate) and the plot is fitted by the power law $\eta = K \gamma^{n-1}$, wherein K is a material constant, $\gamma$ is the shear rate. The reported shear viscosity of the composition herein is an extrapolation to a shear rate of 3000 s$^{-1}$ using the power law relation.

B. Extensional Viscosity

The extensional viscosity is measured using a capillary rheometer (Model Rheograph 2003, manufactured by Goettfert). The measurements are conducted using a semi-hyperbolic die design with an initial diameter ($D_{initial}$) of 15 mm, a final diameter ($D_{final}$) of 0.75 mm and a length (L) of 7.5 mm.

The semi-hyperbolic shape of the die is defined by two equations. Where Z=the axial distance from the initial diameter, and where D(z) is the diameter of the die at distance z from $D_{initial}$;

$$Z_n = (L+1)^{\frac{(n-1)}{n_{total}}} - 1$$

$$D(Z_n) = \sqrt{\frac{(D_{initial}^2)}{\left[1 + \frac{Z_n}{L}\left[\left(\frac{D_{initial}}{D_{final}}\right)^2 - 1\right]\right]}}$$

The die is attached to the lower end of a barrel, which is held at a fixed test temperature (t) which corresponds to the temperature at which the starch composition is to be processed. The test temperature (processing temperature) is a temperature above the melting point of a sample starch composition. The sample starch composition is preheated to the die temperature is loaded into the barrel section of the rheometer, and substantially fills the barrel section. If after the loading, air bubbles to the surface, compaction prior to running the test is used to rid the molten sample of entrapped air. A piston is programmed to push the sample from the barrel through the hyperbolic die at a chosen rate. As the sample goes from the barrel through the orifice die, the sample experiences a pressure drop. An apparent extensional viscosity is calculated from the pressure drop and the flow rate of the sample through the die according to the following equation;

Extensional Viscosity=(delta P/extension rate/$E_h$)·10$^5$ where extensional viscosity is in pascal-seconds, delta P is the pressure drop in bars, extension rate is the flow rate of the sample through the die in sec$^{-1}$, and $E_h$ is dimensionless Hencky strain. Hencky strain is the time or history dependent strain. The strain experienced by a fluid element in a non-Newtonian fluid is dependent on its kinematic history, that is $$\varepsilon = \int_0^t \varepsilon \cdot (t') \partial t'$$

The Hencky Strain ($E_h$) for this design is 5.99 defined by the equation;

$Eh = \ln[(D_{initial}/D_{final})^2]$

The apparent extensional viscosity is reported as a function of extension rate of 250$^{-1}$ using the power law relation. Detailed disclosure of extensional viscosity measurements using a semi-hyperbolic die is found in U.S. Pat. No. 5,357,784, issued Oct. 25, 1994 to Collier, the disclosure of which is incorporated herein by reference.

C. Molecular Weight and Molecular Weight Distribution

The weight-average molecular weight (Mw) and molecular weight distribution (MWD) of starch are determined by Gel Permeation Chromatography (GPC) using a mixed bed column. Parts of the instrument are as follows:

| | |
|---|---|
| Pump | Waters Model 600E |
| System controller | Waters Model 600E |
| Autosampler | Waters Model 717 Plus |
| Column | PL gel 20 μm Mixed A column (gel molecular weight ranges from 1,000 to 40,000,000) having a length of 600 mm and an internal diameter of 7.5 mm. |
| Detector | Waters Model 410 Differential Refractometer |
| GPC software | Waters Millenium ® software |

The column is calibrated with Dextran standards having molecular weights of 245,000; 350,000; 480,000; 805,000; and 2,285,000. These Dextran calibration standards are available from American Polymer Standards Corp., Mentor, Ohio. The calibration standards are prepared by dissolving the standards in the mobile phase to make a solution of about 2 mg/ml. The solution sits undisturbed overnight. Then it is gently swirled and filtered through a syringe filter (5 μm Nylon membrane, Spartan-25, available from VWR) using a syringe (5 ml, Norm-Ject, available from VWR).

The starch sample is prepared by first making a mixture of 40 wt % starch in tap water, with heat applied until the mixture gelatinizes. Then 1.55 grams of the gelatinized mixture is added to 22 grams of mobile phase to make a 3 mg/ml solution which is prepared by stirring for 5 minutes, placing the mixture in an oven at 105° C. for one hour, removing the mixture from the oven, and cooling to room temperature. The solution is filtered using the syringe and syringe filter as described above.

The filtered standard or sample solution is taken up by the autosampler to flush out previous test materials in a 100 µl injection loop and inject the present test material into the column. The column is held at 70° C. The sample eluded from the column is measured against the mobile phase background by a differential refractive index detector held at 50° C. and with the sensitivity range set at 64. The mobile phase is DMSO with 0.1% w/v LiBr dissolved therein. The flow rate is set at 1.0 ml/min and in the isocratic mode (i.e., the mobile phase is constant during the run). Each standard or sample is run through the GPC three times and the results are averaged.

The molecular weight distribution (MWD) is calculated as follows:

$$MWD = \text{weight average molecular weight/number average molecular weight}$$

D. Thermal Properties

Thermal properties of the present starch compositions are determined using a TA Instruments DSC-2910 which has been calibrated with an indium metal standard, which has an melting temperature (onset) of 156.6° C. and a heat of melting of 6.80 calories per gram, as reported in the chemical literature. Standard DSC operating procedure per manufacturer's Operating Manual is used. Due to the volatile evolution (e.g., water vapor) from the starch composition during a DSC measurement, a high volume pan equipped with an o-ring seal is used to prevent the escape of volatiles from the sample pan. The sample and an inert reference (typically an empty pan) are heated at the same rate in a controlled environment. When an actual or pseudo phase change occurs in the sample, the DSC instrument measures the heat flow to or from the sample versus that of the inert reference. The instrument is interfaced with a computer for controlling the test parameters (e.g., the heating/cooling rate), and for collecting, calculating and reporting the data.

The sample is weighed into a pan and enclosed with an o-ring and a cap. A typical sample size is 25–65 milligrams. The enclosed pan is placed in the instrument and the computer is programmed for the thermal measurement as follows:

1. equilibrate at 0° C.;
2. hold for 2 minutes at 0° C.;
3. heat at 10° C./min to 120° C.;
4. hold for 2 minutes at 120° C.;
5. cool at 10° C./min to 30° C.;
6. equilibrate at ambient temperature for 24 hours, the sample pan may be removed from the DSC instrument and placed in a controlled environment at 30° C. in this duration;
7. return sample pan to the DSC instrument and equilibrate at 0° C.;
8. hold for 2 minutes;
9. heat at 10° C./min to 120° C.;
10. hold for 2 minutes at 120° C.;
11. cool at 10° C./min to 30° C. and equilibrate; and
12. remove the used sample.

The computer calculates and reports the thermal analysis result as differential heat flow (ΔH) versus temperature or time. Typically the differential heat flow is normalized and reported on per weight basis (i.e, cal/mg). Where the sample exhibits a pseudo phase transition, such as a glass transition, a differential of the ΔH v. time/temperature plot may be employed to more easily determine a glass transition temperature.

E. Water Solubility

A sample composition is made by mixing the components with heat and stirring until a substantially homogeneous mixture is formed. The melt composition is cast into a thin film by spreading it over a Teflon® sheet and cooling at ambient temperature. The film is then dried completely (i.e., no water in the film/composition) in an oven at 100° C. The dried film is then equilibrated to room temperature. The equilibrated film is ground into small pellets.

To determine the % solids in the sample, 2 to 4 grams of the ground sample is placed in a pre-weighed metal pan and the total weight of pan and sample is recorded. The weighed pan and sample is placed in a 100° C. oven for 2 hours, and then taken out and weighed immediately. The % solids is calculated as follows:

$$\% \text{ Solids} = \frac{(\text{dried weight of ground sample \& pan} - \text{weight of pan})}{(\text{first weight of ground sample \& pan} - \text{weight of pan})} \times 100$$

To determine the solubility of the sample composition, weigh 10 grams of ground sample in a 250 mL beaker. Add deionized water to make a total weight of 100 grams. Mix the sample and water on a stir plate for 5 minutes. After stirring, pour at least 2 mL of stirred sample into a centrifuge tube. Centrifuge 1 hour at 20,000 g at 10° C. Take the supernatant of the centrifuged sample and read the refractive index. The % solubility of the sample is calculated as follows:

$$\% \text{ Soluble Solids} = \frac{(\text{Refractive Index \#}) \times 1000}{\% \text{ Solids}}$$

F. Caliper

Prior to testing, the film sample is conditioned at a relative humidity of 48%–50% and at a temperature of 22° C. to 24° C. until a moisture content of about 5% to about 16% is achieved. The moisture content is determined by TGA (Thermo Gravimetric Analysis). For Thermal Gravimetric Analysis, a high resolution TGA2950 Termogravimetric analyzer from TA Instruments is used. Approximately 20 mg of sample is weighed into a TGA pan. Following the manufacturer's instructions, the sample and pan are inserted into the unit and the temperature is increased at a rate of 10° C./minute to 250° C. The % moisture in the sample is determined using the weight lost and the initial weight as follows:

$$\% \text{ Moisture} = \frac{\text{Start Weight} - \text{Weight@250° C.}}{\text{Start Weight}} * 100\%$$

Preconditioned samples are cut to a size greater than the size of the foot used to measure the caliper. The foot to be used is a circle with an area of 3.14 square inches.

The sample is placed on a horizontal flat surface and confined between the flat surface and a load foot having a horizontal loading surface, where the load foot loading surface has a circular surface area of about 3.14 square inches and applies a confining pressure of about 15 g/square cm (0.21 psi) to the sample. The caliper is the resulting gap between the flat surface and the load foot loading surface. Such measurements can be obtained on a VIR Electronic Thickness Tester Model II available from Thwing-Albert, Philadelphia, Pa. The caliper measurement is repeated and recorded at least five times. The result is reported in mils.

The sum of the readings recorded from the caliper tests is divided by the number of readings recorded. The result is reported in mils.

EXAMPLES

The materials used in the Examples are as follows:

Crystal Gum® is a modified starch having a weight-average molecular weight of 100,000; Nadex® is a modified starch having a weight average molecular weight of 2,000; and Instant-n Oil® is a modified starch having a weight average molecular weight of 800,000; all are available from National Starch and Chemicals Corp., Bridgewater, N.J.

Superfloc® A-130 is a carboxylated polyacrylamide having a weight-average molecular weight of 12,000,000 to 14,000,000 and is available from Cytec Co., Stamford, Conn.

Nonionic polyacrylamides PAM-a and PAM-b having a weight-average molecular weight of 15,000,000, and 5,000,000 to 6,000,000, respectively, are available from Scientific Polymer Products, Inc., Ontario, N.Y.

Polyethyleneimine having a weight-average molecular weight of 750,000 is available from Aldrich Chemical Co., Milwaukee, Wis.

Parez® 631 NC is a low molecular weight glyoxylated polyacrylamide, and Parez® 802 is a low molecular weight glyoxylated urea resin, both are available from Cytec Co., Stamford, Conn.

Pluronic® F87 is nonionic poloxomer, available form BASF corp., Parsippany, N.J.

Urea, sucrose and glyoxal (in 40% solution in water) are available from Aldrich Chemical Co., Milwaukee, Wis.

Example 1

A melt processable composition of the invention is prepared by mixing 45 wt % starch (Crystal Gum), 40.5 wt % urea, 4.5 wt % sucrose, and 9.8 wt % free water, and manually stirring to form a slurry. Polyacrylamide (PAM-a, Mw=15,000,000) is dissolved in water to form a PAM aqueous solution. An aliquot of the polymer/water solution is added to the slurry. Water in the slurry is then evaporated until the weight percent of polyacrylamide in the final mixture is 0.2 wt %.

The composition has a shear viscosity of 0.65 Pa·s and an extensional viscosity of 1863.2 Pa·s, at 700 s$^{-1}$ and 90° C.

Comparative Example 1b

A comparative starch composition is prepared according to Example 1 except no polyacrylamide is added to the composition. The composition has a shear viscosity of 1.35 Pa·s and an extensional viscosity of 43.02 Pa·s, at 700 s$^{-1}$ and 90° C. Example 1 and Comparative Example 1b demonstrate that addition of a small amount of high polymer decreases the shear viscosity slightly and significantly increases the extensional viscosity.

Example 2

A melt processable composition of the invention is prepared by mixing 50 wt % starch (Crystal Gum), 30 wt % urea, 1.5 wt % sucrose, and 18.5 wt % free water, and manually stirring to form a slurry. Polyacrylamide (Superfloc A-130, Mw=12–14,000,000) is dissolved in water to form a PAM aqueous solution. An aliquot of the polymer/water solution is added to the slurry. Water in the slurry is then evaporated until the weight percent of polyacrylamide in the final mixture is 0.003 wt %.

The composition has a shear viscosity of 1.12 Pa·s and an extensional viscosity of 46.0 Pa·s, at 700 s$^{-1}$ and 90° C.

Comparative Example 2b

A comparative starch composition is prepared according to Example 2 except no polyacrylamide is added to the composition. The composition has a shear viscosity of 1.23 Pa·s and an extensional viscosity of 0.69 Pa·s, at 700 s$^{-1}$ and 90° C. Example 2 and Comparative Example 2b demonstrate that addition of a small amount of high polymer decreases the shear viscosity slightly and significantly increases the extensional viscosity.

Example 3

A torque rheometer having a melt blowing die is used to process the composition of Example 1. The torque rheometer is illustrated in FIG. 1. The torque rheometer assembly 100 includes a drive unit 110 (Model Rheocord 90 available from Haake GmbH), a barrel 120 partitioned into four temperature zones 122, 124, 126 and 128, a feed port 121, and a melt spinning die assembly 130. Twin screw elements 160 (model TW100, from Haake GmbH) are attached to the drive unit 110 and disposed within the barrel 120. A six inch wide melt blowing die assembly 130 (available from JM Laboratories, Dawsonville, Ga.) is connected to the end of the barrel via a pump 140. The die assembly has a spinneret plate which has 52 holes per linear inch and a hole diameter of 0.015" (0.0381 cm), surrounded by a 0.02" wide air passageway 152, from which a high velocity air stream 150 impinges the extruded filaments just below the spinneret plate. The air stream has the effect of simultaneously blowing the filaments away from the spinneret and attenuating the filaments.

The composition of is prepared (as described in Example 1) by mixing 45 wt % starch (Crystal Gum), 0.2 wt % polyacrylamide (PAM-a), 40.5 wt % urea, 4.5 wt % sucrose, and 9.8 wt % water. The mixture is gravity-fed via feed port 121 into a torque rheometer. The torque rheometer and die assembly are set as follows:

| Barrel Temperature | |
| --- | --- |
| Zone 122 | 70° C. |
| Zone 124 | 90° C. |
| Zone 126 | 90° C. |
| Zone 128 | 90° C. |
| Torque | 100 rpm |
| Die Temperature | 126.7° C. |
| Air Temperature | 126.7° C. |
| Air Pressure | 35 psi |
| Pump | 40 rpm |

The mixture is conveyed from the extruder through the pump into the melt blowing die. The resulting attenuated filaments (or fine fibers) of the invention have fiber diameters ranging from 8 to 40 microns.

Note that the weight percent starch in the melt processable composition includes the weight of starch and the weight of bound water (which is on the average about 8 wt % of the starch). It is to be understood that the as-prepared compositions are used for uniaxial and biaxial extensional processes. However, most of the water is lost during the melt process, and the resulting starch fiber, film or like product contains little or no free water. The resulting product does contain some bound water (possible by absorbing moisture from ambient environment). Therefore, the composition of the resulting product may be more appropriately expressed by its solid components, calculated on a dry solid basis. For example, to calculate, on a dry solid basis, the composition of the fiber made according to Example 3, one would take out the 9.8 wt % free water from the overall composition and the 8 wt % bound water from the starch, then normalize the remaining solid content to 100%. Thus, the composition of the fiber of Example 3 calculated on a dry solid basis would be 47.8 wt % starch solid (without bound water), 0.23 wt % polyacrylamide, 46.8 wt % urea and 5.2 wt % sucrose.

Example 4

Figure 3A:
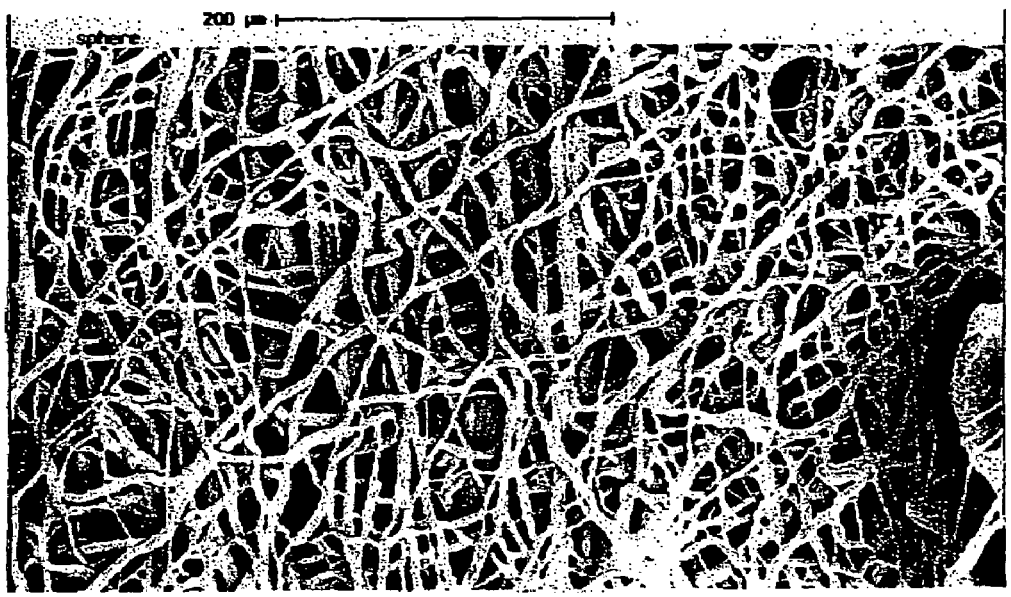
FIG. 3a is the Scanning Electron Micrographs of fine starch fibers of the present invention shown on a 200 micron scale.
Figure 3B:
FIG. 3b is the Scanning Electron Micrographs of fine starch fibers of the present invention shown on a 20 micron scale.

The composition of Example 2 is melt blown into fine fibers of the invention. FIG. 3a is the Scanning Electron Micrographs of fine starch fibers made from the composition of Example 2 using the process described in Example 3, shown on a 200 micron scale. FIG. 3b is the Scanning Electron Micrographs of the same starch fibers shown on a 20 micron scale. Both figures show that starch fibers of Example 4 have a fairly consistent fiber diameter of about 5 microns.

Example 5

Fifteen grams of starch (Crystal Gum, Mw=100,000) and fifteen grams of free water are mixed together at 80° C. with manual stirring until the mixture becomes substantially homogeneous or gelatinizes. A high polymer (PAM-a, Mw-15,000,000) is dissolved in free water to form a PAM aqueous solution of known concentration. An aliquot of the polymer/water solution is added to the starch/water mixture such that the overall mixture contains 0.006 grams of PAM-a. Then the overall mixture is heated to evaporate water until the weight of the final mixture (starch, PAM-a and water) equals 30 grams. This mixture is subjectively shown to have suitable melt extensibility for drawing fibers.

Examples 6–8

Mixtures of starch (Crystal Gum), high polymer and water are prepared in the same manner as in Example 5. The final compositions of these mixture are shown below.

|  |  | Mw |  | Ex-6 | Ex-7 | Ex-8 |
|---|---|---|---|---|---|---|
| Starch | Crystal Gum | 100,000 | wt % | 49.99 | 49.99 | 46.92 |
| Poly-acrylamide | Superfloc A-130 | 12–14,000,000 | wt % | 0.02 |  |  |
|  | PAM-b | 5–6,000,000 | wt % |  | 0.02 |  |
| Polyethyl-eneimine |  | 750,000 | wt % |  |  | 6.17 |
| Water |  |  | wt % | 49.99 | 49.99 | 46.91 |

These compositions of the invention are subjectively shown to have suitable melt extensibility for drawing fibers.

Examples 9–11

The following compositions are prepared in the same manner as Example 1.

|  |  | Mw |  | Ex-9 | Ex-10 | Ex-11 |
|---|---|---|---|---|---|---|
| Starch | Crystal Gum | 100,000 | wt % | 41.54 | 20.77 | 20.77 |
|  | Nadex | 2,000 | wt % |  | 20.77 |  |
|  | Instant-n Oil | 800,000 | wt % |  |  | 20.77 |
| Poly-acrylamide | PAM-a | 15,000,000 | wt % | 0.08 | 0.08 | 0.08 |
| Urea |  |  | wt % | 6.23 | 6.23 | 6.23 |
| Sucrose |  |  | wt % | 6.23 | 6.23 | 6.23 |
| Parez 631 NC |  |  | wt % | 1.04 | 1.04 | 1.04 |
| Water |  |  | wt % | 44.88 | 44.88 | 44.88 |

These compositions of the invention are expected to have suitable melt extensibility for drawing fibers. And where the water has been adjusted to about pH 2, the resulting fibers are expected to have a water solubility of less than 30%, based on the test method disclosed herein.

Example 12

A melt processable composition is prepared by mixing 45 wt % starch (Crystal Gum), 0.2 wt % polyacrylamide (PAM-a), 40.5 wt % urea, 4.5 wt % sucrose, and 9.8 wt % water to form a slurry. The composition is melt blown into fine fibers using a torque rheometer as shown in FIG. 1 in the manner described in Example 3, except the mixture is meter-fed into the torque rheometer. The torque rheometer and die assembly are set as follows:

| Barrel Temperature |  |
|---|---|
| Zone 122 | 70° C. |
| Zone 124 | 90° C. |
| Zone 126 | 90° C. |
| Zone 128 | 90° C. |
| Torque | 140 rpm |
| Feed Rate | 16 gm/min |
| Die Temperature | 137.8° C. |
| Air Temperature | 137.8° C. |
| Air Pressure | 50 psi |
| Pump | 40 rpm |

The resulting attenuated filaments (or fine fibers) of the invention have fiber diameters ranging from 10 to 30 microns. The fibers are air laid onto a papermaking forming fabric as described in U.S. Pat. No. 4,637,859, with the fabrics of U.S. Pat. Nos. 5,857,498, 5,672,248, 5,211,815 and 5,098,519, all incorporated herein by reference, also being judged suitable for this purpose.

Example 13

The resultant web from the air-laying process of Example 12 is tested for oil absorbency. A drop of a commercially available motor oil (SAE 20 grade, by the Society of Automobile Engineers' designation) is placed on the web and on a commercially available paper towel, respectively, for comparison of oil absorbency. The web shows an improved oil absorbency over that of the commercial paper towel in the following aspects: (1) the web absorbs oil faster than the commercial paper towel, as shown by a shorter residence time on the surface of the web; and (2) after 30 seconds, the web has a spot size of about 1.5 to 2 times larger in diameter than that of the commercial paper towel.

Example 14

This example illustrates that the starch composition of the present invention can be made into building materials, e.g., pressed board. A melt processable composition is prepared by mixing 60 wt % starch (Crystal Gum), 0.1 wt % polyacrylamide (SP2), 2 wt % urea, 2 wt % sucrose, 1.5 wt % Parez 631 NC and 34.4 wt % water (adjusted to pH 2 with sulfuric acid) to form a slurry. The slurry is fed in to a torque rheometer (Model Rheocord 90) as illustrated in FIG. 1 and operated under the conditions as described in Example 12 above, except a single capillary die (having a 1 mm diameter and a temperature of 90° C.) is used instead of a melt spinning die. The extruded strand is dusted with saw dust or wood shavings while still wet and sticky. The dusted strands are compressed together to form a log. The log is dried at 40° C. in a forced air oven for two hours to get rid of the residual water from the starch composition. The final product is a log of 47.8 wt % saw dust and 52.2 wt % dried starch composition.

Example 15

Starch Solution Preparation

A solution of modified starch in water is prepared by mixing 275 grams of Purity Gum 59 (from National Starch Co., a waxy maize starch with the weight average molecular weight reduced to approximately 330,000 daltons), 10 grams of anhydrous glycerol, 0.5 grams of anhydrous sodium sulfate and 214.5 grams of distilled water. The mixture is heated on a hot plate to about 60° C. with handmixing to dissolve the starch and is then placed in a 70° C. oven overnight.

Meltblowing of Starch Fibers

The starch solution is placed in the reservoir of a ram extruded which is temperature controlled by a heat tape to stay within the range of from about 120–200° F. The solution is delivered to an air atomizing nozzle manufactured by Spraying System (hereinafter alternatively referred to as "the nozzle" or "the die") and is extruded through the nozzle at a flow of 1.2 cm$^3$/minute at a solution temperature of 50° C. The inner diameter of the nozzle is 0.014 inches.

The solution forms a downward-pointed jet as it emerges from the nozzle. The nozzle arrangement allows an air stream to be fed concentrically around the solution jet emerging from the nozzle. The air stream emerges from a gap between the nozzle outer diameter of 0.050 inches and an air cap of 0.180 inches. The air cap is fed with humid air at up to 20 psi. The humid air is created by mixing a heated air line and a 40 psi steam source to produce the desired temperature and humidity. The relative flowrates and temperatures are controlled to yield humidities of 30–100% and temperatures of 120 to 200 F. The humid air delivered to the air cap is directed downward to provide an attenuation drag force.

The solution jet is then dried by air from a pair of ducts. A pair of rectangular ducts, 2" wide and 0.050" high supply the drying air. The air ducts are oriented so that the width is perpendicular to the falling solution jet. The two air streams are directed inward toward the filament and downward. The drying ducts are positioned adjacent to the nozzle. The two air streams intersect the solution jet 2" below the nozzle tip. The air stream is drawn from a compressed air line and fed through an air heater. The heater can raise the temperature up to 500° F., to promote drying. The compressed air line can deliver up to 40 SCFM of air at pressures up to 60 psi.

The attenuation air temperature is 70° C., the attenuation air relative humidity is 90%, the attenuation air flow rate is 9 cubic feet per minute. The drying air temperature is 200° C. and the drying air flow rate is approximately 45 cubic feet per minute. A web of starch is collected. An SEM photomicrograph of the starch fiber web is shown in FIG. 1. Based on a measurement of 40 fibers, the average fiber diameter is 7.8 microns with a standard deviation of 2.5 microns. Fiber diameters in the web ranged from a minimum of 4.4 microns to a maximum of 16.6 microns. The capillary number for the starch solution under these meltblowing conditions is calculated to be 7.7 based on a shear viscosity of 2.7 pascal seconds, and a surface tension of 70 dynes per centimeter. The apparent extensional viscosity, as measured with a semi-hyperbolic capillary die, for the starch solution at 50° C. is 400 pascal seconds.

While particular embodiments of the present invention have been illustrated and described, it would be obvious to those skilled in the art that various other changes and modifications can be made without departing from the spirit and scope of the invention.

The invention claimed is:

1. A composition comprising a starch, wherein said composition has an extensional viscosity in the range of from about 50 pascal•seconds to about 20,000 pascal•seconds and wherein said composition exhibits a capillary number of at least 1.

2. The composition of claim 1 wherein the starch has a molecular weight ranging from about 1,000 to about 2,000,000 and wherein from about 20 to about 99 wt % of the starch is amylopectin.

3. The composition of claim 2 wherein the capillary number ranges from about 1 to about 100.

4. The composition of claim 3 wherein said composition comprises from about 70% to about 95% by weight of the composition of the starch and from about 5% to about 30% by weight of the composition of an additive and wherein said composition has an extensional viscosity in the range of from about 100 pascal•seconds to about 15,000 pascal•seconds.

5. The composition of claim 4 wherein the composition is processed at a temperature ranging from about 80° C. to about 180° C.

6. The composition of claim 3 wherein said composition comprises from about 40% to about 70% by weight of the composition of the starch and from about 30% to about 60% by weight of the composition of an additive and wherein said composition has an extensional viscosity in the range of from about 100 pascal•seconds to about 15,000 pascal•seconds.

7. The composition of claim 6 wherein the composition is processed at a temperature ranging from about 80° C. to about 140° C.

8. The composition of claim 6 wherein said composition has an extensional viscosity in the range of from about 200 pascal•seconds to about 10,000 pascal•seconds and a capillary number in the range of from about 3 to about 50.

9. The composition of claim 8 wherein said composition has an extensional viscosity in the range of from about 300 pascal•seconds to about 5000 pascal•seconds and a capillary number ranging from about 5 to about 30.

10. The composition of claim 9 which has a Trouton ratio in the range of from about 3 to about 10,000 when measured at 90° C. and 700 s$^{-1}$.

11. The composition of claim 10 wherein the weight average molecular weight of the starch ranges from about 2,000 to about 500,000.

12. The composition of claim 11 wherein the composition comprises from about 45 to about 65% by weight of the composition of the starch and from about 35% to about 55% by weight of the composition of the additive.

13. The composition of claim 12 wherein the additive comprises water.

14. A fiber, filament foam and/or film prepared by a process comprising:
  (1) forming a composition comprising:
    (a) from about 5% to about 99.99% by weight of the compositions of a starch, wherein the starch has a weight-average molecular weight ranging from about 1,000 to about 2,000,000; and
    (b) from about 0.001% to about 95% by weight of the composition of an additive selected from the group consisting of plasticizers and diluents; and
  (2) passing said composition, which has a capillary number of at least 1, through a die to produce the fiber, filament foam and/or film.

15. A composition comprising a starch, wherein said composition exhibits a capillary number of at least 1.

16. A process for making a fiber from a starch composition comprising a starch, wherein said process comprises the step of spinning the starch composition into a fiber, wherein the starch composition exhibits a capillary number of at least 1.

* * * * *